United States Patent [19]
Siconolfi

[11] Patent Number: 5,948,977
[45] Date of Patent: Sep. 7, 1999

[54] SOFT-SIDED AIR DISPLACEMENT VOLUMOMETER

[75] Inventor: Steven F. Siconolfi, Grosse Pointe Pk., Mich.

[73] Assignee: The United States of America as represented by the United States National Aeronautics and Space Administration, Washington, D.C.

[21] Appl. No.: 09/054,311

[22] Filed: Mar. 31, 1998

[51] Int. Cl.⁶ ................................................. G01F 17/00
[52] U.S. Cl. ................................................................ 73/149
[58] Field of Search ............................................... 73/149

[56] References Cited

U.S. PATENT DOCUMENTS

| | | | |
|---|---|---|---|
| 4,448,207 | 5/1984 | Parrish | 128/771 |
| 4,589,280 | 5/1986 | Carter | 73/226 |
| 4,778,451 | 10/1988 | Kamen | 604/67 |
| 5,054,316 | 10/1991 | Pratt et al. | 73/149 |
| 5,092,170 | 3/1992 | Honstvet et al. | 73/295 |
| 5,157,968 | 10/1992 | Zfira | 73/149 |
| 5,272,920 | 12/1993 | Stephenson et al. | 73/301 |
| 5,319,964 | 6/1994 | Stephenson et al. | 73/149 |
| 5,359,977 | 11/1994 | Abbey | 123/452 |
| 5,377,538 | 1/1995 | Cardinal | 73/118.2 |
| 5,410,916 | 5/1995 | Cook | 73/706 |
| 5,450,750 | 9/1995 | Abler | 73/149 |

FOREIGN PATENT DOCUMENTS

| | | | |
|---|---|---|---|
| 0611119 | 6/1978 | U.S.S.R. | 73/149 |

*Primary Examiner*—Robert Raevis
*Attorney, Agent, or Firm*—James M. Cate

[57] ABSTRACT

A soft-sided air displacement volumometer includes a soft-sided bag, an air injector, a pressure transducer, and a recording device. The soft-sided volumometer is used to measure the total body volume of a person or the volume of one limb of a person. After the person enters the soft-sided bag, the bag is sealed and pressurized to a predetermined level using the air injector. The pressure inside the soft-sided bag is continuously monitored using the pressure transducer and recording device while the volume of the soft-side bag is incrementally reduced. The elasticity of the soft-sided bag is eliminated from the volume calculations by operating the soft-sided air displacement volumometer over a relatively small range of volumes and pressures in which the elasticity is substantially constant. The volume of the person inside the soft-sided bag is calculated as the volume of the empty bag (i.e. without a person) minus the initial volume of the bag with the person pressurized to an initial pressure level.

25 Claims, 4 Drawing Sheets

SOFT-SIDED AIR DISPLACEMENT VOLUMOMETER

ORIGIN OF THE INVENTION

The invention described herein was made by employee(s) of the United States Government and may be manufactured and used by or for the Government of the United States of America for governmental purposes without the payment of any royalties thereon or therefor.

BACKGROUND OF THE INVENTION

1. Field of the Invention

The present invention relates generally to an apparatus and method for measuring the volume of a body or other solid object. Still more particularly, the present invention relates to a body volume measurement technique using a soft-sided bag.

2. Background of the Invention

A complete evaluation of a person's physical condition includes a physical examination as well as other assessments. For many patients it is desirable to assess the patient's percent body fat, bone mineral content, and volume of water. For example, by measuring or estimating the mineral content of a person's bones, various skeletal disorders such as osteoporosis can be monitored and appropriate treatment can be prescribed. Further, for long duration space flight in which an astronaut's muscles and bones naturally atrophy from reduced usage, it is important to evaluate, and preferably minimize, the magnitude and extent of the atrophy. A determination of body composition aids in this evaluation.

A crude body composition model of a person includes a fat component (also referred to as a "compartment") and a lean body mass component (non-fat mass). A three-compartment model has also been suggested for modeling body composition. The three-compartment model includes a fat compartment, a dry lean mass compartment, and a water compartment (typically referred to as "total body water").

Various techniques have been suggested for measuring body composition. For example, in one technique, measurements of the body's electrical impedance are used to estimate total body water using regression equations.

The two-compartment model comprising lean body mass and fat mass usually is determined by measuring a patient's total mass (typically measured in units of kilograms) and total body volume (measured in units of liters). On the ground, mass is determined from a recording of a person's weight. Determining mass in this manner in the near weightless environment in which an astronaut works does not work. Numerous other techniques for measuring an astronaut's mass have been suggested and attempted.

The standard technique for measuring a patient's total body volume has been underwater weighing (also referred to as "hydrostatic weighing"), a technique based on Archimides' Principle. Using this technique, the difference between a subject's weight out of water and the subject's weight submersed in water is measured. The subject's body volume equals the volume of water displaced by the subject once submersed in the water. The volume of water displaced is determined by calculating the volume of water corresponding to the difference in the person's weight in and out of water. Although generally accurate, the underwater weighing technique requires complete submersion of the person in water and maximal expulsion of air from the person's lungs and measuring the residual volume left in the lungs.

Submersion of some patients may be impossible because of the patient's condition. Subject movements, incomplete lung emptying, and variability in lung measurements affect the accuracy of the resulting measurement. Further, some patients are afraid of submersion in water. Additionally, this technique cannot be used during space flight.

Hard-sided volumometers have been used to measure total body volume. These devices are based on Boyle's gas law in which the product of the volume of a gas multiplied by its pressure is a constant value at a fixed temperature. A hard-sided volumometer is a rigid chamber large enough to hold a patient. The person's body volume is measured by measuring the pressure in the chamber while the volume of the chamber is varied, and applying Boyle's Law to the resulting pressure measurements. Hard-sided volumometers have not been used extensively because their accuracy is usually less than desirable. Further, hard-sided volumometers generally are not portable making their use for many patient's impractical. Where weight and volume are at a premium such as in space, hard-sided volumometers are too bulky and heavy to be feasible. Finally, underwater weighing systems and hard-sided volumometers are very costly.

Thus, an accurate, portable, and inexpensive volumometer for measuring a person's total body volume is needed. Such a device could easily be used in a variety of situations including hospitals, doctors' offices, health clubs, space flight, and the like.

SUMMARY OF THE INVENTION

The present invention includes a method and apparatus for solving the deficiencies of the prior art to measure total body volume or the volume of a single limb by including a soft-sided bag, an air injector, a pressure transducer, and a recording device. The air injector and pressure transducer couple via hoses to ports on the soft-sided bag. The pressure transducer couples to the recording device. The pressure transducer provides an electrical signal that is a function of the air pressure inside the bag. The recording device records the electrical signal from the pressure transducer to enable an operator to determine the pressure of the air inside the bag. The air injector pumps air into the soft-sided bag and the pressure transducer and recording device monitor the pressure inside the bag. The bag is large enough to allow a person to stand or lie inside. Using this system and performing the method below, the volume of the subject can be determined.

A method for determining the volume of a subject includes placing the subject inside the soft-sided bag, sealing the bag, and pressurizing the bag using the air injector to an initial pressure level. During the measurement cycle, the subject must hold his or her breath and nose to avoid distorting the data. One end of the bag is compressed (i.e., rolled up) to a first position and the pressure inside the bag is determined at that position. The bag is further compressed to a second position and the pressure is again determined. Alternatively, the pressure inside the bag at the first and second compression positions can be determined after the measurement cycle is complete.

As the bag is compressed, the volume inside the bag reduces and the pressure increases. The first and second compression positions are selected to cause pressure and volume changes within a predetermined range of values. Within this pressure and volume range, the elasticity of the soft-sided bag is substantially constant, thereby making the volume computations relatively simple.

As an alternative embodiment to the pressure transducer and recording device, a control unit including a pressure transducer, controller, air pump, flow meter, and display device may be used for automatically making volume measurements.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of a preferred embodiment of the present invention, reference will now be made to the accompanying drawings, wherein.

DETAILED DESCRIPTION OF A PREFERRED EMBODIMENT

Figure 1:
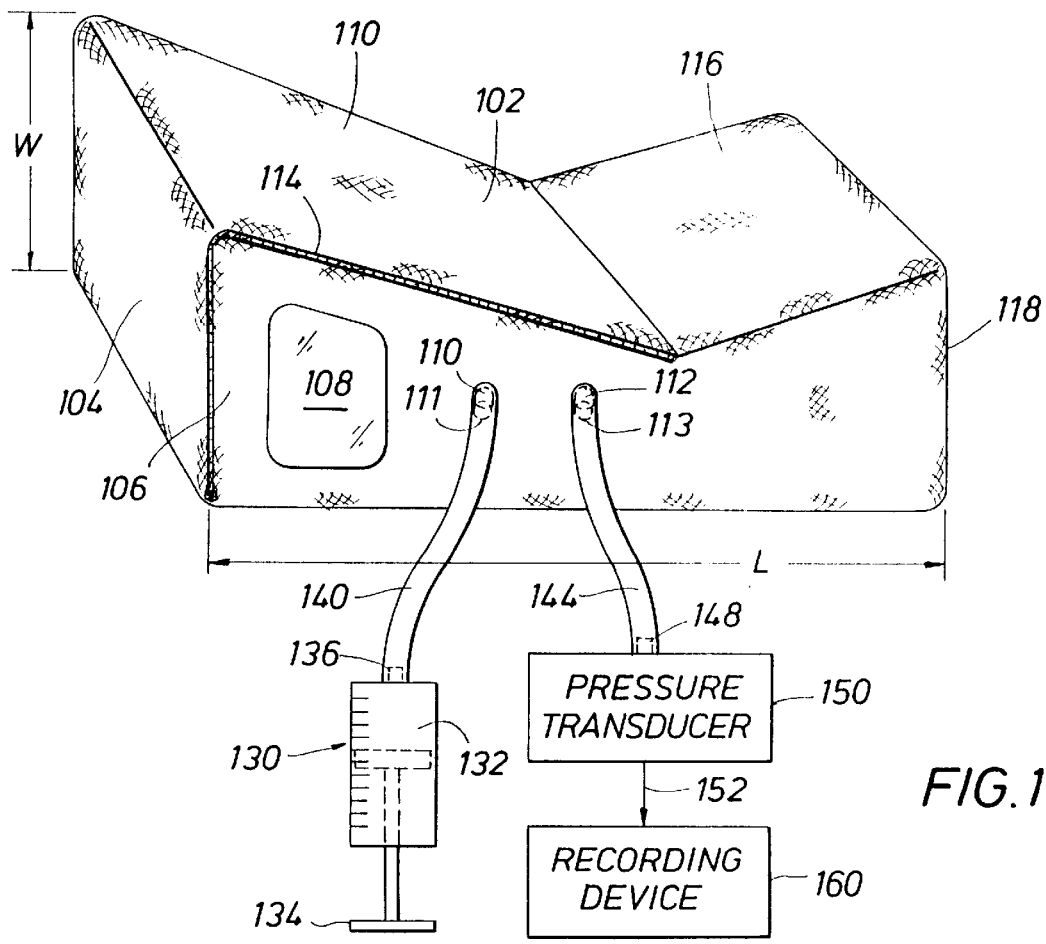
FIG. 1 is soft-sided volumometer constructed in accordance with a preferred embodiment along with a pressure transducer, recording device, and pressure injector.

Referring now to FIG. 1, a soft-side air displacement volumometer system 100 constructed in accordance with a preferred embodiment generally includes a soft-sided bag 102, an air injector 130, a pressure transducer 150, and recording device 160. The air injector 130 connects to a port 110 on the soft-sided bag 102 via a hose 140. Similarly, the pressure transducer connects to a second port 112 on the soft-sided bag via hose 144.

The soft-sided bag 102 preferably is constructed of a flexible material, such as nylon or other suitable flexible and lightweight material. Preferably the material is coated with polyurethane to help seal and reduce the elasticity of the material.

Although the shape of the soft-sided bag 102 includes the shape shown in FIG. 1, other shapes are acceptable as well, such as a cylindrical shape. The soft-sided bag 102 preferably is large enough to accommodate a large adult. In accordance with a preferred embodiment, the bag 102 is approximately 102 inches long (dimension L) and 36 inches wide (dimension W).

The soft-sided bag 102 includes a top surface 104, side surfaces 106, front surfaces 110 and 116 and a bottom surface 118. A zipper 114 or other fastening mechanism allows a subject to enter the bag 102 or allow the bag to placed around the subject, as might be necessary for a bed-ridden patient. The patient can be viewed through a transparent window 108 formed in the side surface 106 of the bag 102. The zipper 114 and all other seams in the soft-sided bag 102 preferably provide air tight seals.

In accordance with a preferred embodiment, the soft-sided bag 102 can collapse down on itself or otherwise be folded into a relatively small volume for ease of storage and portability. This portability advantageously facilitates using the soft-sided volumometer system 100 at various locations for measuring total body volume. The preferred method and apparatus described below for measuring total body volume can also can be used to measure the volume of a single limb as will be apparent once the preferred embodiment of the invention is understood.

Connections to the soft-sided bag 102 are provided through ports 110 and 112 which preferably provide a communication path between the inside volume of the bag 102 and the region outside the bag. Ports 110, 112 are provided with standard access stems 111 and 113, respectively, bonded to the bag 102 or otherwise attached in an appropriate manner. Preferably ports 110, 112 are provided with identical access stems to allow air injector 130 and the pressure transducer 150 to be connected to either port. Accordingly, the soft-sided bag can be inflated by connecting an air pressure source, such as injector 130, to either port 110 or 112 and the air pressure inside the bag can be measured by connecting a pressure transducer also to either port. However, if it is desired that the ports should not be interchangeable for injecting air and monitoring pressure, different size and shape access stems can be used. Alternatively, standard connectors can be used in place of access stems.

Referring still to FIG. 1, the air injector 130 includes any device for injecting a predetermined volume of air into the soft-sided bag. The injector may be a commonly known Tissot that includes a cylinder 132 and a plunger 134, configured similar to a syringe. Graduated markings on the sided of the cylinder 132 indicate the volume of gas delivered from or drawn into the injector 130. Hose 140 from the injector 130 frictionally fits over the access stem 111 of port 110, thereby coupling injector 130 to port 110. The opposite end of hose 140 fits over the tip 136 of the injector 130. The hose 140, as well as hose 144, are constructed of plastic or other suitable material.

Pressure transducer similarly 150 couples to port 112 of soft-sided bag 102 via hose 144. One end of hose 144 frictionally fits over access stem 113 of port 112, and the other end of the hose 144 fits over an inlet port 148 of pressure transducer 150. Alternatively, pressure transducer 150 may couple directly to port 112, thereby obviating the need for hose 144. Although a number of commercially available pressure transducers are acceptable, the pressure transducer 150 preferably has an accuracy level of approximately 1 milliliter of water (1 mil $H_2O$) or less. This level of accuracy is preferred to enable the soft-sided volumometer system 100 to provide an overall accuracy level of ±0.15%. A differential pressure transducer manufactured by Iomega generally is suitable for the present invention.

According to known principles, the pressure transducer 150 generates an output electrical signal that is representative of the pressure of the air on its inlet port 148. Generally, the magnitude of the voltage of the output signal is a direct function of the magnitude of the air pressure. In accordance with the preferred embodiment, the output signal from transducer 150 comprises an analog signal that varies according to the pressure on inlet port 148, and thus the pressure of the air inside the soft-sided bag 102.

Pressure transducer 150 couples to a recording device 160 via electrical lines 152. The recording device 160 may include any suitable recording device such as an electrostatic printed or plotter, digital storage device, and the like. The recording device 160 records the transducer's output signal received via lines 152. The recording device 160 is used to determine the magnitude of the air pressure of the bag 102. For example, if the recording device 160 includes a printer or plotter, in which an analog pressure waveform is printed on paper, the pressure of the bag 102 can be measured by measuring the height of the pressure waveform printed by the recording device 160. Alternatively, if a digital storage device is used as the recording device, the recording device 160 may display the pressure reading calibrated to the appropriate units of pressure. Regardless of the type of recording device used, it is important that the air pressure inside the bag 102 be determined in some manner. Unless otherwise indicated, the following discussion assumes the recording device includes a printer or plotter that provides a strip-chart style printout of the air pressure inside the soft-sided bag 102 as a function of time.

The operation of the soft-sided volumometer will now be described with reference first to FIGS. 1 and 2. FIGS. 2a–2c schematically illustrate how the soft-sided volumometer is used to measure the total body volume of a person 170. Although the bag 102 and person 170 are illustrated in a supine position in FIGS. 2a–2c, the bag 102 can also be used with the person 170 standing upright as well. After the person 170 enters the soft-sided bag 102, the bag is sealed using a pressure zipper 114 (FIG. 1). Using the air injector 130, the soft-sided bag 102 is pressurized to an initial pressure level determined from pressure transducer 150 and recording device 160. For example, an initial pressure level of 10 centimeters of water (10 cm $H_2O$) is acceptable, although other initial pressure levels are acceptable as well. While the subject holds his breath and closes his nose, the soft-sided bag 102 is compressed to a first level 119 as shown in FIG. 2b. The soft-sided bag 102 is compressed by rolling up the bottom portion 118 to the first level 119 which may be identified by markings on the soft-sided bag 102. With the bag compressed to the first point 119, the pressure inside the bag is determined from the transducer 150 and recording device 160. Then, the soft-sided bag 102 is compressed to the second level 121 as shown in FIG. 2c and another pressure reading is taken. It is important for the subject to hold his breath and close his nose to ensure an accurate volume measurement.

As will be seen below, the preferred method for measuring volume of a person only requires knowing the initial pressure in the soft-sided bag 102 (10 cm $H_2O$, for example) and measuring the air pressure inside the bag with the bag compressed or rolled up to two different compression positions 119 and 121 shown in FIGS. 2a–2c. As the bag 102 is compressed, the volume and pressure of the bag change. Compression positions 119 and 121 are selected to cause a change in the bag's pressure and volume within a certain range of values, as will become apparent from the discussion that follows.

Because the person 170 must hold his or her breath during the measurement cycle, the measurement cycle should be completed as quickly as possible, preferably in less than 10 seconds. Accordingly, the pressure of the bag 102 when the bag is compressed to compression positions 119 and 121 preferably is determined after the measurement cycle is completed. Thus, the pressure transducer 150 and recording device 160 preferably continuously monitor and record the pressure of the air inside the soft-sided bag 102 during the measurement cycle so that the data can be processed after the measurement cycle is complete. An indicator, such as a momentary pause while rolling up the bottom portion 118 of the bag 102, on the paper printout of the pressure signal is useful to indicate when the bag 102 was compressed to levels 119, 121. Alternatively, some printers and plotters include a feature that allows a user to press a key thereby simultaneously causing the printer or plotter to print a mark on the printout. Such a key could be pressed when the bag is compressed to levels 119 and 121.

Figure 2A:
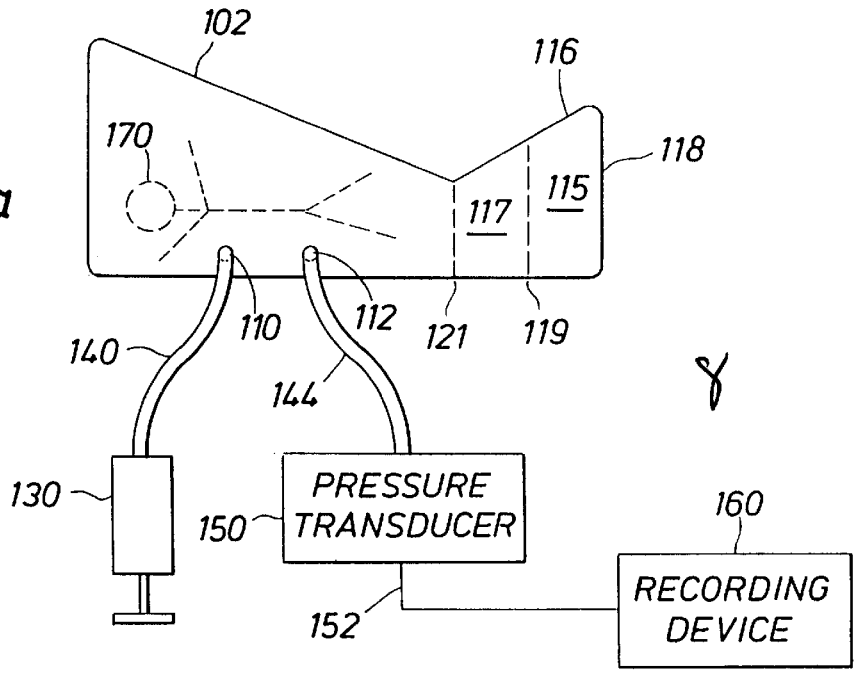
FIGS. 2a–2c illustrate the technique of measuring a person's total body volume using the soft-sided volumometer of FIG. 1.
Figure 2B:
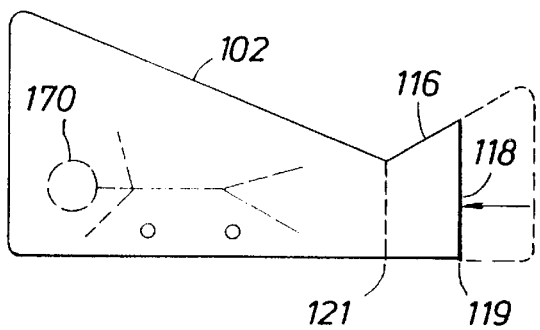
Figure 2C:
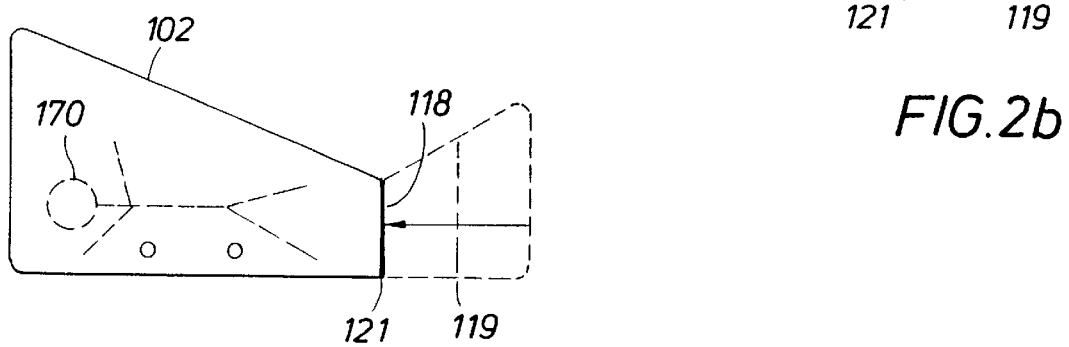
Figure 3:
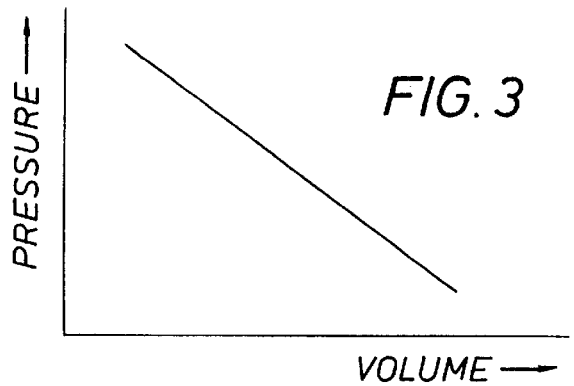
FIG. 3 is an exemplary pressure-volume graph of a hard-sided, inelastic chamber.

Referring now to FIGS. 2 and 3, the preferred technique for determining total body volume will be further described. According to Boyle's gas law, the product of pressure and volume inside a chamber is a constant value. Thus, as the chamber's volume is increased, the pressure inside the chamber must decrease. Similarly, as the chamber's volume decreases, the pressure inside the chamber must increase. This relationship between pressure and volume is illustrated in the graph of FIG. 3 in which pressure is shown on the vertical axis and volume is shown on the horizontal axis. The pressure-volume relationship in FIG. 3 is linear (a straight line) which would be the case for a hard-sided chamber in which the walls of the chamber are inelastic (i.e., the walls do not stretch as pressure increases).

Figure 4:
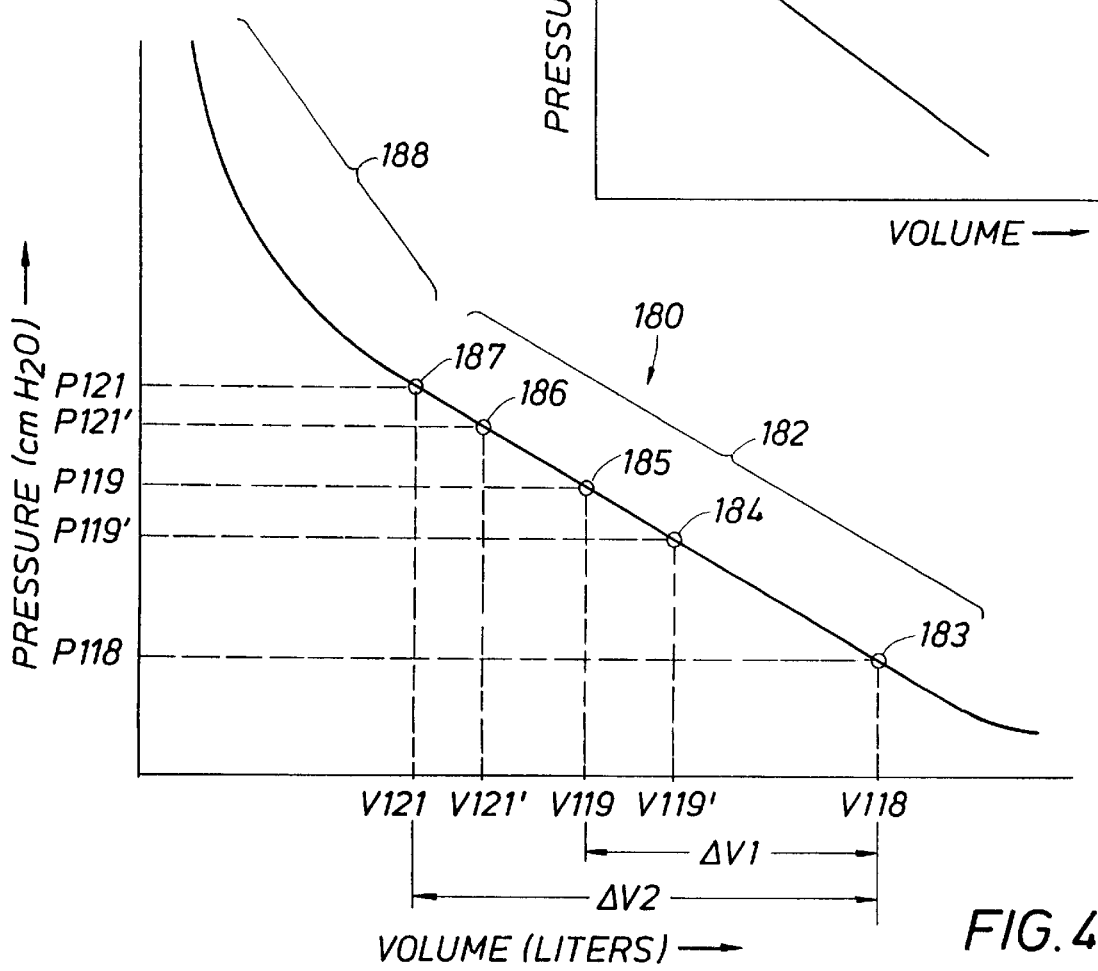
FIG. 4 reflects the pressure-volume relationship of the soft-sided volumometer of FIG. 1.

Referring now to FIG. 4, an exemplary pressure-volume relationship 180 of the soft-sided bag 102 is shown. Because the soft-sided bag 102 is made out of a flexible material, there is a certain amount of elasticity to the material causing the material to stretch and the soft-sided bag 102 to expand outward as the pressure inside the bag increases. The elasticity of the material comprising the soft-sided bag 102 causes the volume of the bag to be greater than it otherwise would be if it were a hard-sided, inelastic chamber. Accordingly, the pressure-volume relationship of the soft-sided bag 102 is non-linear (i.e., curved). Non-linear curve 180 generally includes a curved portion 188 in which the amount of elasticity varies and a substantially linear portion 182 in which the amount of elasticity is relatively constant. In accordance with a preferred embodiment of the invention, the soft-sided volumometer system 100 is operated along substantially linear portion 182 so that the elasticity can be assumed to be a constant value.

Point 183 on the pressure-volume relationship 180 identifies the pressure and volume corresponding to the soft-sided bag 102 in its fully expanded, initially pressurized position as in FIG. 2a. Accordingly, volume V118 reflects the volume of air in the soft-sided bag 102 and the pressure P118 is the pressure of the air inside the soft-sided bag 102 in its initial position. If the bag 102 is initially pressurized to 10 cm $H_2O$, pressure P118 will equal 10 cm $H_2O$. Points 184 and 186 on response 180 represent the pressures and volumes of the bag 102 when compressed to compression positions 119 and 121 (FIGS. 2b, 2c). Thus, pressure P119' and volume V119' represent the pressure and volume of the soft-sided bag 102 compressed to position 119 (FIG. 2b). Pressure P121' and volume V121' represent the pressure and volume of bag 102 compressed to position 121 (FIG. 2c). Point 185 represents the pressure and volume of the bag compressed to point 119, if the bag had been a hard-sided, inelastic chamber. The pressure of point 185 (P119) is greater, and the volume is less, than the actual pressure and volume at point 184 (P119' and V119') because the volume, had the bag been inelastic, would have been less resulting in, per Boyle's Law, higher pressure. Similarly, point 187 represents the pressure, P121, and the volume, V121, had the bag been inelastic and compressed to position 121 (FIG. 2c) had the bag been inelastic. The soft-sided volumometer system 100 preferably is operated within the linear portion 182 of the pressure-volume relationship 180. Accordingly, elasticity can be assumed constant simplifying the calculation of body volume.

To determine the volume of the person 170 inside the soft-sided bag 102, the initial volume V118 of air in the bag 102 with pressure at the initial pressure level must be determined. The initial volume V118 can be determined from the following equation:

$$V118 = \frac{\Delta V2 - \Delta V1}{(P118/P119') - (P118/P121')} \quad (1)$$

where –V2 represents the difference in volume between V118 and V121, and –V1 represents the difference in volume between V118 and V119 (i.e., the change in volume of the bag 102 as it was compressed had the bag been a hard-sided, inelastic chamber). The volume values –V1 and –V2 are constants and can be calculated using standard principles of geometry or other known techniques. The volume –V1 represents the volume of that portion of the bag (assuming no elasticity) rolled up in compressing the bag to compression position 119 (identified with reference number 115 in FIG. 2a). Similarly, the volume –V2 represents the volume of that portion of the bag (still assuming no elasticity) rolled up in compressing the bag to compression position 121 from the initial, uncompressed position. The volume –V2 includes the sum of the volumes identified by reference numbers 115 and 117 in FIG. 2a.

Once V1 is known, the total body volume of person 170 can be calculated as:

$$V_{person} = \text{volume of empty bag} - V1 \quad (2)$$

where the volume of the empty bag represents the volume of the bag pressurized to 10 centimeters of water without a person inside the bag. The volume of the empty bag can be determined at any time before the body volume measurement is made and preferably need be determined only once. The empty bag volume can be measured by injecting a known volume of air into an evacuated bag 102 until the pressure inside the bag reaches the initial pressure level used in the measurement of total body volume (e.g., 10 cm $H_2O$). The empty bag volume is a constant value that is used for all body volume measurements. However, the empty bag volume can be remeasured at any time, if desired. Further, the foregoing method can be repeated multiple times each time calculating the volume of the person. The total body volumes can then be averaged together, thereby improving overall accuracy.

Figure 5:
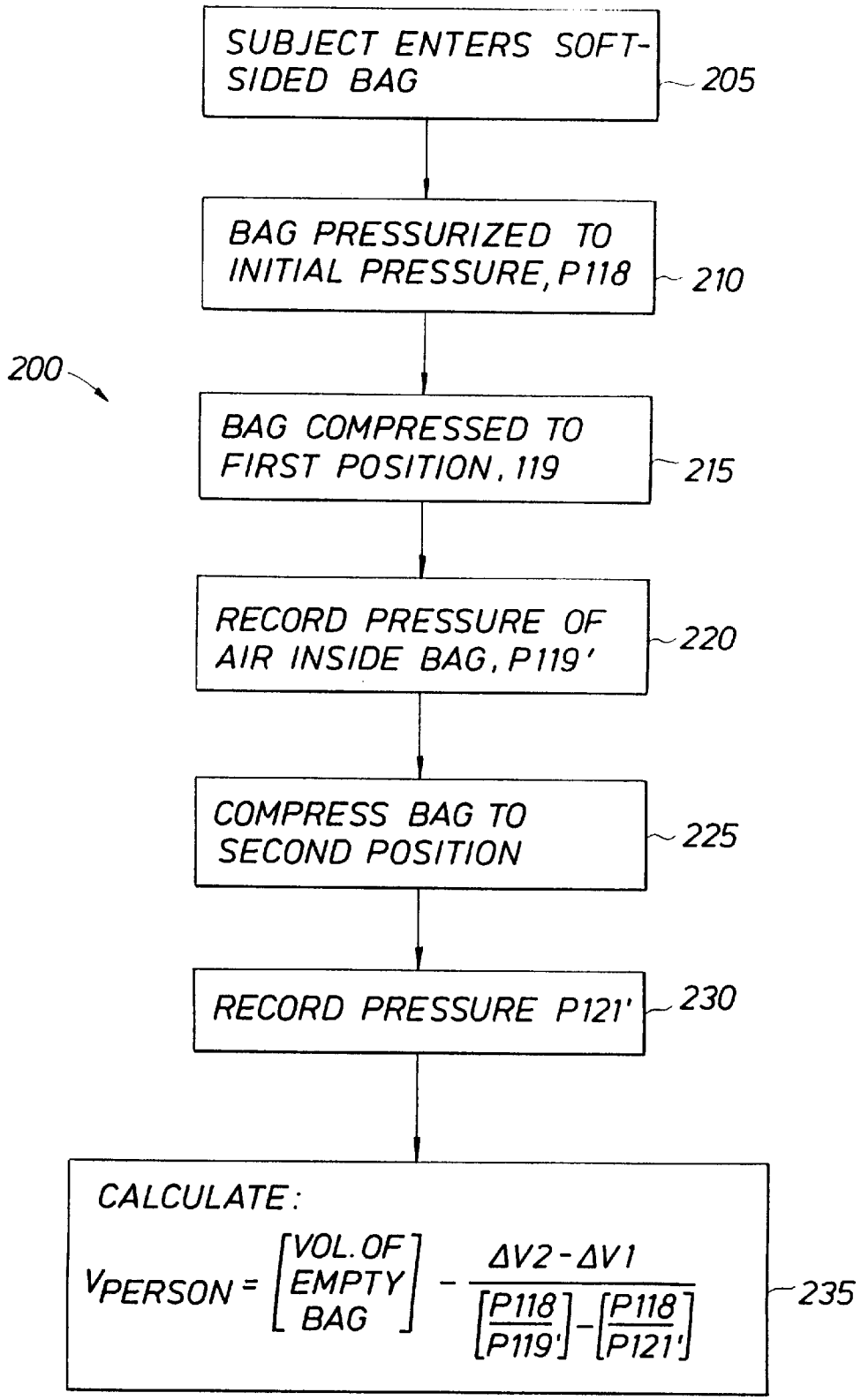
FIG. 5 illustrates a preferred method for determining a person's volume.

Referring now to FIG. 5, the preferred method for calculating total body volume is shown in flow chart 200. In step 205, the subject enters the soft-sided bag 102 and the bag is sealed shut by the zipper 114 (FIG. 1). The soft-sided bag 102 is then pressurized to an initial pressure level of, for example, 10 centimeters of water using air injector 130 (step 210). In step 215, the soft-sided bag 102 is compressed to the first level 119 and the resulting pressure, P119, is measure in step 220. In step 225, the bag 102 is compressed to the second level 121, and in step 230, the pressure P121' is recorded. Finally, in step 235 the volume of the person is calculated using equation (1).

Steps 210–235 may be repeated multiple times to obtain multiple body volume determinations. The body volumes may then be averaged together to reduce error in any one measurement. Further, as discussed previously, instead of recording the pressures P119' and P121' in steps 220 and 230 during a measurement cycle, a continuous pressure signal can be recorded by the recording device 160, and the pressure values can be determined after method cycle 200 has been completed.

Figure 6:
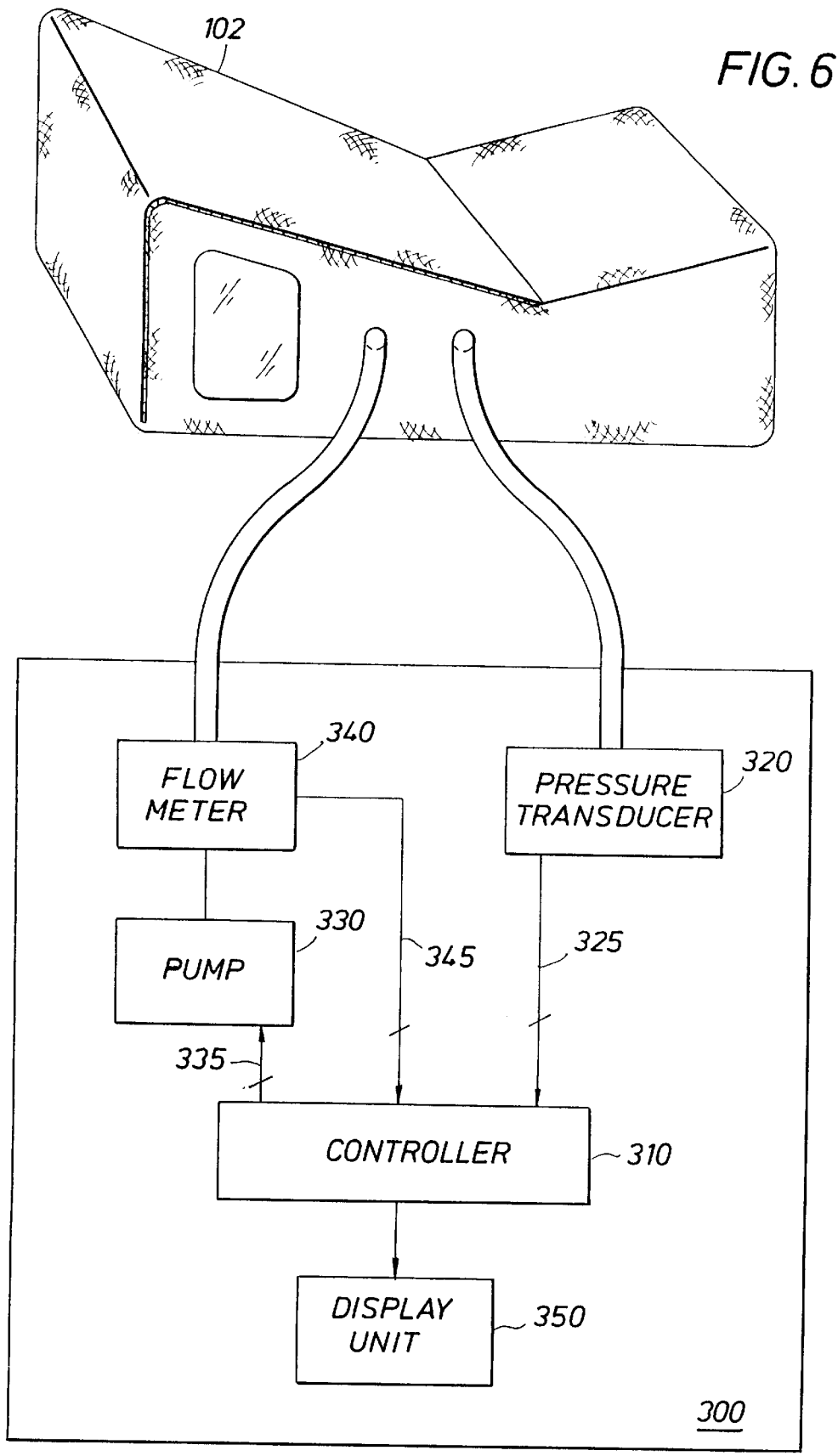
FIG. 6 is an alternative embodiment of the soft-sided volumometer system of FIG. 1 in which the recording device is replaced with a control system.

Referring now to FIG. 6, an alternative embodiment to the soft-sided air displacement volumometer system 100 of FIG. 1 includes a control unit 300 for automatically making body volume measurements. The control unit 300 may include off the shelve components or comprise a custom designed assembly. In accordance with the alternative embodiment, the control unit 300 includes a controller 310, a pressure transducer 320, a pump 330, a flow meter 340, and a display unit 350. The pressure transducer 320 provides an electrical signal to controller 310 via lines 325 representing the pressure of the air inside the soft-sided bag 102. Via control lines 335, the controller 310 turns the pump 330 on and off and controls the volume of air pumped into the soft-sided bag 102. The controller 310 also may vary the speed at which the pump 330 operates to control the rate at which the pressure inside the soft-sided bag 102 changes. Flow meter 340 monitors the volume of air flowing through the transducer 340 and provides an electrical signal back to the controller 310 via lines 345. Status, configuration, and measurement data are displayed by controller 310 on display unit 350.

Once the subject enters the soft-sided bag 102, the control unit 300 can be activated by a user, and the measurements preferably will be made automatically. An operator will still need to compress one end of the soft-sided bag, but the control unit 300 will automatically determine the pressure inside the bag at the appropriate compression points. Further, the control unit 300 can be programmed to compute the subject volume using equation (1) above. The resulting calculated total body volume may then be displayed on display unit 350.

The soft-sided air displacement volumometer system advantageously measures body volume to an accuracy of approximately ±0.15%. Further, the soft-sided air displacement volumometer system is lightweight and portable and thus can be used in a variety of situations including bedridden or immobile patients as well as astronauts in the near weightless environment of space flight.

Numerous variations and modifications will become apparent to those skilled in the art once the above disclosure is filly appreciated. It is intended that the following claims be interpreted to embrace all such variations and modifications.

What is claimed is:

1. A volumometer system, comprising:
    a soft-sided bag in which a subject volume to be measured is placed;
    an air injector coupled to said soft-sided bag;
    a pressure transducer coupled to said soft-sided bag; and
    a recording device coupled to said pressure transducer.

2. The volumometer system of claim 1, wherein said soft-sided bag includes at least two ports to which said air injector and said pressure transducer couple.

3. The volumometer system of claim 2, wherein an end portion of said soft-sided bag is compressible to permit a volume measurement to be made of the subject volume inside the bag.

4. The volumometer system of claim 3, wherein said end portion of said soft-sided bag is compressible to at least two different positions to permit the making of said volume measurement.

5. The volumometer system of claim 4, wherein said soft-sided bag includes an opening through which said subject volume enters and exits said soft-sided bag.

6. The volumometer system of claim 5, wherein said opening includes a substantially air-tight seal.

7. The volumometer system of claim 6, wherein said seal includes a zipper.

8. The volumometer system of claim 7, wherein said subject volume includes a person.

9. The volumometer system of claim 7, wherein said subject volume includes a person's limb.

10. The volumometer system of claim 7 wherein said air injector includes a Tissot.

11. A volumometer system, comprising:
 a soft-sided bag in which a subject volume to be measured is placed, said soft-sided bag including at least two ports and a re-sealable zippered opening through which said subject volume enters and exits;
 a Tissot coupled to one of said at least two ports on said soft-sided bag;
 a pressure transducer coupled to another of said at least two ports on said soft-sided bag; and
 a recording device coupled to said pressure transducer;
 wherein an end portion of said soft-sided bag is compressible to one of at least two different positions.

12. A method for measuring the volume of a subject, comprising:
 placing the subject into a soft-sided bag;
 sealing the subject inside the soft-sided bag;
 pressurizing the soft-sided bag to an initial pressure level;
 compressing the soft-sided bag to a first position;
 compressing the soft-sided bag to a second position; and
 calculating the volume of the subject.

13. The method of claim 12, further including determining a second pressure inside the soft-sided bag when said bag is compressed to said first position.

14. The method of claim 13, further including determining a third pressure inside the soft-sided bag when said bag is compressed to said second position.

15. The method of claim 14, wherein said step of calculating said volume uses said initial pressure, second pressure, and third pressure.

16. The method of claim 15, wherein said step of calculating said volume also includes determining the volume of the interior of said soft-sided bag when said soft-sided bag is pressurized to said initial pressure level.

17. A method for measuring the volume of a subject, comprising:
 placing the subject into a soft-sided bag;
 sealing the soft-sided bag while the subject remains in said soft-sided bag;
 pressurizing the soft-sided bag to an initial pressure level;
 compressing the soft-sided bag to a first position;
 compressing the soft-sided bag to a second position;
 determining a second pressure inside said soft-sided bag when said bag is compressed to said first position;
 determining a third pressure inside said soft-sided bag when said bag is compressed to said second position; and
 calculating the volume of the subject using said initial, second, and third pressures and the volume of the interior of said bag when said bag is pressurized to said initial pressure.

18. A volumometer system, comprising:
 a soft-sided bag in which a subject volume to be measured is placed;
 an air injector coupled to said soft-sided bag;
 a control unit including a pressure transducer coupled to a controller.

19. The volumometer system of claim 18, wherein said control unit also includes an air pump and a flow meter, and wherein said air pump couples to said controller and said flow meter couples said air pump to said soft-sided bag.

20. The volumometer system of claim 19, wherein said control unit also includes a display device for displaying status, configuration and volume information.

21. The volumometer system of claim 20, wherein said soft-sided bag includes a plurality of ports.

22. The volumometer system of claim 21, wherein said flow meter and said pressure transducer couple to said ports on said soft-sided bag.

23. The volumometer system of claim 22, wherein said controller controls the rate at which said air pump introduces air into said soft-sided bag.

24. The volumometer system of claim 23, wherein said soft-sided bag includes a re-sealable opening through which said subject volume enters and exits said soft-sided bag.

25. A volumometer system, comprising:
 a soft-sided bag in which the subject volume to be measured is placed, said bag including first and second ports and a re-sealable opening through which the subject volume enters and exits said bag;
 a control unit including:
  a controller;
  an air pump coupled to said controller;
  a flowmeter coupled to said air pump and said first port on said soft-sided bag;
  a pressure transducer coupled to said controller and to said second port on said soft-sided bag; and
  a display unit for displaying status, configuration, and volume information;
  wherein said controller controls the rate at which said air pump introduces air into said soft-sided bag.

* * * * *